US005955259A

United States Patent [19]
Holmes et al.

[11] Patent Number: 5,955,259
[45] Date of Patent: Sep. 21, 1999

[54] METHOD FOR ASSESSING MODULATION OF POTASSIUM ION CHANNEL ACTIVITY

[75] Inventors: Todd C. Holmes, Somerville; Irwin B. Levitan, Newton, both of Mass.

[73] Assignee: Brandeis University, Waltham, Mass.

[21] Appl. No.: 08/769,745

[22] Filed: Dec. 19, 1996

[51] Int. Cl.$^6$ ............................. C12Q 1/00; G01N 33/53
[52] U.S. Cl. ................................ 435/4; 435/7.1; 435/7.8
[58] Field of Search ................................ 530/350; 435/4, 435/7.1, 7.8

[56] References Cited

U.S. PATENT DOCUMENTS

5,541,109   7/1996   Searfoss et al. ..................... 435/252.3

OTHER PUBLICATIONS

Holmes et al. (Proc. Ann. Mett. Soc. Neurosci, 1996, 22:1252).
Burgess et al (J. Cell Bio, 1990, 111:2129–2138).
Lazar et al. (Mol. & Cell Biol., 8:1247–1252, 1988).
Tao et al. (J. Immunol, 143:2595–2601, 1989).
Weng et al. (Mol. & Cell Biol, 1994, 14:4509–4521).
Levitzki, A. and Gazit, A., "Tyrosine Kinase Inhibition: An Approach to Drug Development," *Science*, 267: 1782–1788 (1995).
McKay, M. C., et al., "Opening of Large–Conductance Calcium–Activated Potassium Channels by the Substituted Benzimidazolone NS004," *Journal of Neurophysiology*, 71(5): 1873–1882 (1994).
Chandy, K. G., "Simplified gene nomenclature," *Nature*, 352: 26 (1991).
Swanson, R., et al., "Cloning and Expression of cDNA and Genomic Clones Encoding Three Delayed Rectifier Potassium Channels in Rat Brain," *Neuron*, 4: 929–939 (1990).
Slamon, D. J., et al., "Studies of the HER–2/neu Proto–oncogene in Human Breast and Ovarian Cancer," *Science*, 244: 707–712 (1989).
Stühmer, W., et al., "Molecular basis of functional diversity of voltage–gated potassium channels in mammalian brain," *The EMBO J.*, 8: 3235–3244 (1989).
Attali, B., et al., "Regulation of a major cloned voltage––gated K$^+$ channel from human T lymphocytes," *FEBS* 11121, 303(2,3): 229–232 (1992).
Douglass, J., et al., "Characterization and Functional Expression of a Rat Genomic DNA Clone Encoding a Lymphocyte Potassium Channel," *The J. of Immunology*, 144(12): 4841–4850 (1990).
Chandy, K. G., et al., "A Family of Three Mouse Potassium Channel Genes with Intronless Coding Regions," *Science*, 247: 973–975 (1990).
Grissmer, S., et al., "Expression and chromosomal localization of a lymphocyte K$^+$ channel gene," *PNAS USA*, 87: 9411–9415 (1990).
Butler, A., et al., "A Family of Putative Potassium Channel Genes in Drosophila," *Science*, 243: 943–947 (1989).
Kupper, J., et al., "Intracellular and extracellular amino acids that influence C–type inactivation and its modulation in a voltage–dependent potassium channel," *Pflügers Arch— Euro J. Physiol.*, 430: 1–11 (1995).
Busch, A. E., et al., "An Amino Acid Mutation in a Potassium Channel That Prevents Inhibition by Protein Kinase C," *Science*, 255: 1705–1707 (1992).
Culver, K. W., et al., "In Vivo Gene Transfer with Retroviral Vector–Producer Cells for Treatment of Experimental Brain Tumors," *Science* 256: 1550–1552 (1992).
Marom, S. and Levitan, I. B., "State–Dependent Inactivation of the Kv3 Potassium Channel," *Biophysical J.*, 67: 579–589 (1994).
Bowlby, M. R., and Levitan, I. B., "Block of Cloned Voltage–Gated Potassium Channels by the Second Messenger Diacylglycerol Independent of Protein Kinase C," *J. Neurophysiol.*, 73: 2221–2229 (1995).
Qu, Z., et al., "Regulation of Tyrosine Phosphorylation of the Nicotinic Acetylcholine Receptor at the Rat Neuromuscular Junction," *Neuron*, 2: 367–378 (1990).
Cai, Y. –C. and Douglass, J., "In Vivo and in Vitro Phosphorylation of the T Lymphocyte Type n (Kv1.3) Potassium Channel," *J. of Biological Chem.*, 268(31): 23720–23727 (1993).
Keating, M.T. and Sanguinetti, M.C., "Molecular Genetic Insights Into Cardiovascular Disease," *Science*, 272: 681–685 (May 1996).
Levitan, I.B., "Modulation of Ion Channels by Protein Phosphorylation and Dephosphorylation," *Annu. Rev. Physiol.*, 56: 193–212 (1994).
McNicholas C.M., et al., "Regulation of ROMK1 K$^+$ Channel Activity Involves Phosphorylation Processes," *Proc. Natl. Acad. Sci., USA.*, 91: 8077–8081 (1994).
Reinhart, P.H., et al., "Modulation of Calcium–Activated Potassium Channels from Rat Brain by Protein Kinase A and Phosphatase 2A," *J. Neurosci.*, 11: 1627–1635 (1991).

(List continued on next page.)

*Primary Examiner*—Lila Feisee
*Assistant Examiner*—Susan Ungar
*Attorney, Agent, or Firm*—Hamilton, Brook, Smith & Reyonlds, P.C.

[57] ABSTRACT

The present invention relates to a method for assessing the ability of a compound to modulate the formation of a complex between a potassium channel and a protein tyrosine kinase. The method comprises the steps of (1) contacting a first polypeptide comprising the proline-rich binding region of the potassium channel, a second protein comprising the SH3 binding domain of the protein tyrosine kinase and the compound to be assessed; and (2) measuring the extent of complex formation between the first polypeptide and the second polypeptide.

6 Claims, 1 Drawing Sheet

OTHER PUBLICATIONS

Cohen, G.B., et al., "Modular Binding Domains in Signal Transduction Proteins," *Cell* 80: 237–249 (Jan. 1995).

Ren, R., et al., "Identification of a Ten–Amino Acid Proline–Rich SH3 Binding Site," *Science*, 259: 1157–1161 (Feb. 1993).

Maignan, S., et al., "Crystal Structure of the Mammalian Grb2 Adaptor," *Science*, 268: 291–293 (Apr. 1995).

Rickles, R.J., et al., "Identification of Src, Fyn, Lyn, P13K and Ab1 SH3 Domain Ligands Using Phage Display Libraries," *EMBO, J.*, 13: 5598–5604 (1994).

Fields, et al., "The Two–Hybrid System: an assay for protein–protein interactions," *Trends in Genetics* 10: 286–292 (1994).

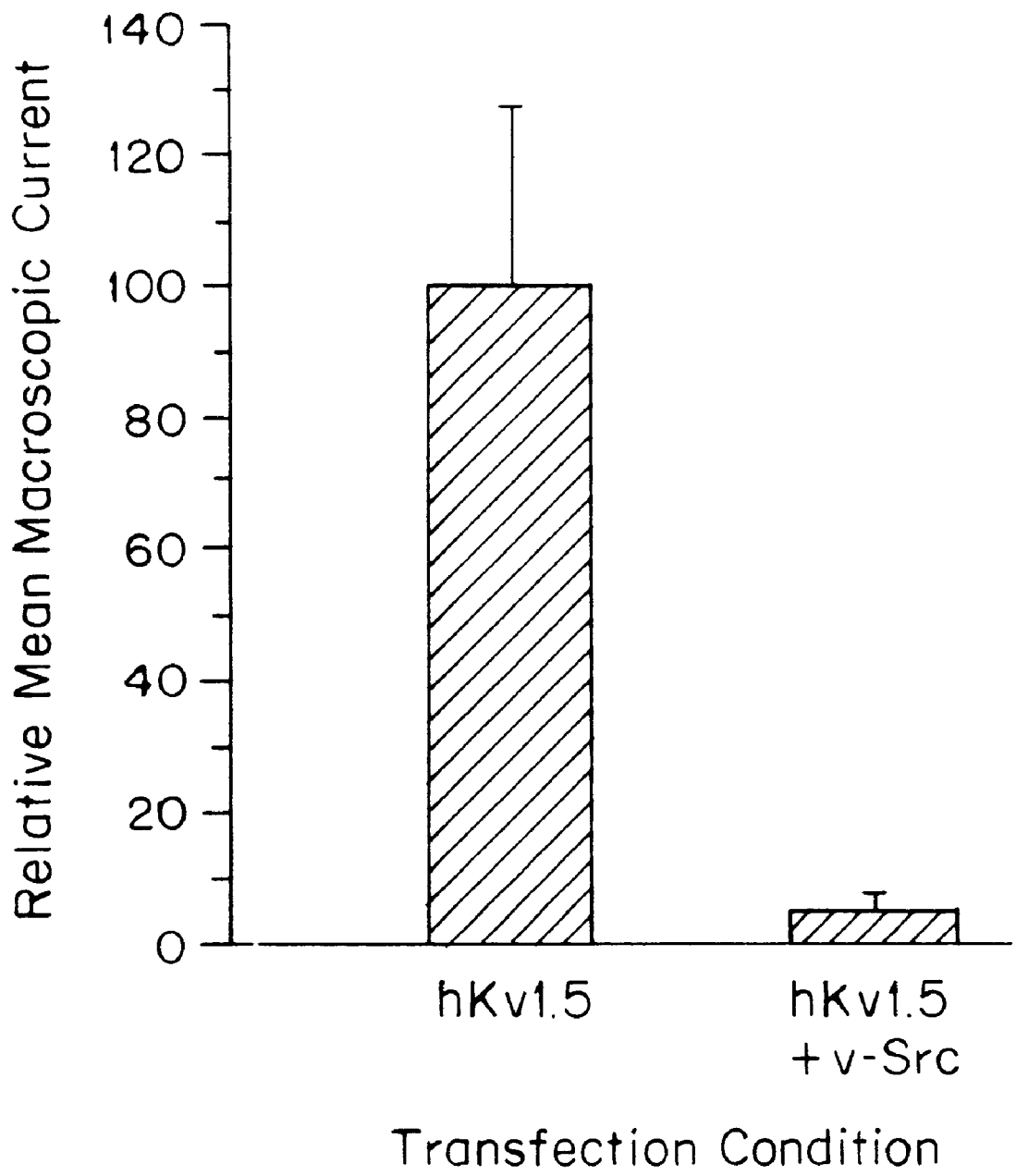
The Figure

METHOD FOR ASSESSING MODULATION OF POTASSIUM ION CHANNEL ACTIVITY

FUNDING STATEMENT

The invention described herein was supported in whole or in part by Grant No. R01 NS17910 from the National Institutes of Health and by a National Institutes of Health Training Grant. The government has certain rights in the invention.

BACKGROUND OF THE INVENTION

Ion channels are proteins which regulate the passage of ions across cell membranes (Hille, *Ionic Channels of Excitable Membranes* Sunderland, Mass., Sinauer Associates (1984)). As ions carry charge, ion channels are important mediators of fundamental cell electrical properties, including the cell resting potential. Ion channel activity is defined as the passage of ions through the channel. The activity of ion channels regulates dynamic electrical events such as depolarization and hyperpolarization. Such dynamic cellular electrical events are critical for a wide variety of physiological processes, including neuronal signaling, control of heart rate, muscle contraction and secretion. Thus, treatments which affect the activity of ion channels, in turn, regulate many physiological processes.

The importance of ion channels for normal physiological function is underscored by studies of mutations in genes which code for ion channels. Such mutations have been implicated in pathological states. In particular, mutations in ion channel genes expressed in the heart result in long QT syndrome, a potentially fatal cardiac arrhythmic disorder (Keating, M. T., et al., *Curr. Opin. Gen. Dev.,* 6: 326–333 (1996); Deal, K. K., et al., *Physiol. Revs.,* 76: 49–67 (1996); Keating, M. T., et al., *Science,* 272: 681–685 (1996)), and central nervous system ion channel mutations result in episodic ataxia (Adleman, J. P., et al., *Neuron.,* 15: 1449–1454 (1995)). Mutations in skeletal muscle ion channels result in movement disorders. For example, mutation of the KCNA gene is associated with myokymia, a condition characterized by sudden loss of coordination and tremor of the head and limbs (Gutmann, L. et. al., *Neurology,* 47: 18–21 (1996)).

Pharmacological studies provide further evidence for the involvement of ion channels in pathological disorders. The anti-histamine drugs terfenadine and astemizole can induce long QT syndrome and cardiac arrhythmia (Woosley, R. L., *Annu. Rev. Pharmacol. Toxicol.,* 36: 233–252 (1996)). The mechanism of toxicity of these drugs is due to cardiac potassium channel blockage, including potassium channels which are disrupted in the inherited cardiac arrhythmia disorder described above (Keating, M. T., et al., *Science,* 272: 681–685 (1996)). Myokymia can be induced by 4-aminopyridine, a potassium channel blocker (Gutmann, L. et. al., *J. Neurology,* 47: 18–21 (1996)). Although these studies provide insights towards understanding the mechanisms underlying these diseases, inherited and drug-induced pathologies (Keating, M. T., et al., *Science,* 272: 681–685 (1996)) account for a small minority of total cases. Cardiac arrhythmia is associated with most of the 250,000 sudden cardiac deaths in the United States each year. However, only a small of fraction of the affected individuals have inherited cardiac arrhythmia or suffer from drug-induced pathology. Thus, it is necessary to search for other causes of ion channel blockage which would contribute to such pathologies.

There is, therefore, a need for an improved understanding of mechanisms of potassium channel blockage. Also needed are methods of assessing the ability of a potential therapeutic agent to inhibit the blockage of a potassium channel.

SUMMARY OF THE INVENTION

The present invention relates to a method for assessing the ability of a compound to modulate the formation of a complex between a potassium channel and a protein tyrosine kinase. The method comprises the steps of (1) contacting a first polypeptide comprising the proline-rich binding region of the potassium channel, a second polypeptide comprising the SH3 binding domain of the protein tyrosine kinase and the compound to be assessed; and (2) measuring the extent of complex formation between the first polypeptide and the second polypeptide. In one embodiment the first polypeptide is incubated with the compound to be assessed before addition of the second polypeptide. In another embodiment, the second polypeptide is incubated with the compound to be assessed before addition of the first polypeptide. The method is carried out in solution, preferably aqueous solution, such as a cell lysate or an aqueous buffer.

The first polypeptide can be any polypeptide comprising an amino acid sequence corresponding to the proline-rich binding sequence of the potassium channel, including the potassium channel itself, a fragment thereof, or a fusion protein comprising the potassium channel or a fragment thereof in conjunction with an additional polypeptide.

The second polypeptide can be any polypeptide comprising an amino acid sequence which corresponds to the SH3 domain of the protein tyrosine kinase. Included are the intact protein tyrosine kinase, a fragment thereof and fusion proteins which include the protein tyrosine kinase or a fragment thereof in conjunction with an additional polypeptide.

In one embodiment, the invention relates to a method for assessing the ability of a compound to modulate the formation of a complex between Src and hKv1.5. The method comprises the steps of (1) contacting a first polypeptide comprising the proline-rich binding sequence of hKv1.5, a second polypeptide comprising the SH3 domain of Src and the compound to be assessed; and (2) measuring the extent of binding of the first polypeptide and the second polypeptide.

The invention further includes compounds which are shown by the method to modulate the binding of a protein tyrosine kinase to an ion channel.

In another embodiment, the invention includes a method of treating an ion channel-mediated condition in an animal, such as a human, by administering to the animal a therapeutically effective amount of a compound which, as shown by the method disclosed above, modulates the binding of a protein tyrosine kinase to an ion channel.

The present method offers several advantages. Applicants have discovered a novel mechanism by which protein tyrosine kinases bind to potassium channels, ultimately leading to channel blockage. This mechanism serves as the basis for the invention disclosed herein, a novel method of screening potential drugs which inhibit the binding of the protein tyrosine kinase, thereby increasing or maintaining ion conduction through the channel and alleviating pathological conditions in which decreased potassium ion conductance has been implicated.

BRIEF DESCRIPTION OF THE DRAWING

The FIGURE is a graph of relative potassium ion current in cells transfected with hKv1.5 (normalized to 100%) and in cells transfected with both hKv1.5 and v-Src.

DETAILED DESCRIPTION OF THE INVENTION

Ion channels fall into two broad classes: voltage-gated channels and ligand-gated channels (Hille, B., *Ionic Channels of Excitable Membranes.* Sunderland, Mass., *Sinauer Associates* (1984)) and (Hille, B., *Neuron,* 9: 1987–195 (1992)). Voltage-gated channels change their activity in response to changes in the electrical potential across the cell membrane in which they reside. Ligand-gated channels change their activity in response to the binding of small molecules. Such channels are also referred to as receptors, based on their binding properties. Extracellular ligands such as neurotransmitters or hormones can bind to the extracellular surface of the channel/receptor. The glutamate N-methyl-d-aspartate receptor is representative of extracellular ligand-gated channel/receptors. In contrast, intracellular signaling molecules, such as second messengers, bind to the intracellular surface of intracellular ligand-gated channel/receptors. Intracellular ligand-gated channels are found in both the plasma membrane, which forms the limit of the cell, and the membranes of internal organelles. The inositol trisphosphate receptor is representative of intracellular ligand-gated channel receptors. While some ion channels are purely voltage- or ligand-gated, some ion channels are influenced by both voltage changes and ligand binding. For example, calcium-activated potassium channels are voltage activated, but calcium binding markedly increases their response to voltage.

The activity of ion channels is subject to another form of regulation called modulation (Levitan, I. B., *Annu. Rev. Physiol.,* 56: 193–212 (1994)). Modulation refers to changes in the channel activity by cellular signals other than voltage changes or ligand binding. Ion channel phosphorylation on serine, threonine or tyrosine residues is a ubiquitous mechanism of modulation. Protein phosphorylation is catalyzed by enzymes called protein kinases. Ion channel activity can be increased (McNicholas, C. M., et al., *Proc. Natl. Acad. Sci., USA.,* 91: 8077–8081 (1994)) or decreased (Reinhart, P. H., et al., *J. Neurosci.,* 11:1627–1635 (1991)) by phosphorylation. Modulatory events by the phosphorylation of serine and threonine channel residues has long been recognized. In contrast, the importance of tyrosine phosphorylation has only recently been discovered. Several factors account for this relatively recent discovery. The vast majority of protein phosphorylation occurs at serine and threonine residues (over 97%). Additionally, the total activity of tyrosine phosphatases to tyrosine kinases is about 1000:1 (Hunter, T., *Cell,* 80: 225–236 (1995)). The consequence of this is that the tyrosine residues are rapidly dephosphorylated, unless phosphatase inhibitors are present in biological preparations. Until the recent development of phosphotyrosine antibodies and other technical improvements, protein tyrosine phosphorylation was relatively difficult to detect.

Ion channels are targets of protein tyrosine kinases and their activity can dramatically change when they are phosphorylated by protein tyrosine kinases. Despite the emerging evidence concerning the functional effects of tyrosine phosphorylation of potassium channels, there is no information available about the mechanisms of targeting and association of channels and protein tyrosine kinases. The existence of signaling complexes consisting of ion channels and closely associated protein kinases and phosphatases has been inferred from functional electrophysiological studies (McNicholas, C. M., et al., *Proc. Natl. Acad. Sci., USA.,* 91: 8077–8081 (1994); Reinhart, P. H., et al., *J. Neurosci.,* 11: 1627–1635 (1991); Chung, S. K., et al., *Science,* 253: 560–562 (1991); Bielefeldt, K., et al., *Biophys. J.,* 66: 1904–1914 (1994); and Rosenmund, C., et al., *Nature* (London), 368: 853–856 (1994)). These inferences are made by the observation of channel "rundown" or runup" in physiological preparations and the sensitivity of such preparations to ATP or pharmacological inhibitors of protein kinases and phosphatases. It is difficult to draw any conclusions as to what proteins may be involved in these putative channel-kinase signaling complexes because pharmacological agents such as ATP and the protein kinase and phosphatase inhibitors used in these studies will interact with many proteins. Biochemical characterization of channel-kinase signaling complexes using specific antibodies to demonstrate cellular colocalization or physical association would be useful, but this has not been demonstrated directly. Additionally, there is no rational basis for screening for the identity of proteins participating in these channel-kinase signaling complexes.

Specific protein-protein interactions between signaling proteins are mediated by modular binding domains (Cohen, G. B., et al., *Cell,* 80: 237–248 (1995). Among the best characterized are the conserved amino acid sequences found in the protein tyrosine kinase, "Src". These sequences are referred to as the Src homology 2 (SH2) and Src homology 3 (SH3) domains. Different SH3 domains bind to proline-rich regions in partner proteins. The core SH3 binding motif consists of the amino acid sequence P—X—X—P (SEQ ID NO:1), in which P is proline and the amino acids at the X positions are less critical for selection. SH3 domains prefer certain proline-rich sequences over others, based on the sequences flanking the P—X—X—P motif. For example, sequences which bind well to the Abl SH3 domain bind poorly to the Src SH3 domain (Rickles, R. J., et al., *EMBO, J.,* 13: 5598–5604 (1994). The preferred sequences for a particular SH3 domain can be derived from examination of the sequences of known binding partners, structural information from X-ray crystallographic and NMR solution structures and combinatorial library selection (Ren, R., et al., *Science,* 259: 1157–1161 (1993); Maignan, S., et al., *Science,* 268: 291–293 (1995) and Rickles, R. J., et al., *EMBO, J.,* 13: 5598–5604 (1994)).

The present invention is based on the discovery that the protein tyrosine kinase Src targets the hKv1.5 potassium channel by the binding of a specific Src domain, the SH3 domain, to a specific proline-rich binding region of the potassium channel. Src catalyzes the phosphorylation of one or more tyrosine residues of the potassium channel, which in turn causes blockage of the channel.

Several species isoforms of the potassium channel hKv1.5, including those from human (hKv1.5), canine and rabbit contain 1 to 2 copies of the preferred Src SH3 domain binding sequence Arg—Pro—Leu—Pro—X—X—Pro (SEQ ID NO:2), where X is generally a proline or a hydrophobic amino acid, such as leucine, valine, alanine, isoleucine, methionine, phenylalanine or tryptophan. The rat isoform of hKv1.5, however, lacks one of the critical proline residues.

Example 1 describes studies directed to determining whether hKv1.5 and Src are associated in vivo. The potassium channel and Src were coexpressed in human embryonic kidney (HEK) 293 cells and tested for their interaction by immunoprecipitation, followed by protein immunoblotting with antibodies specific to hKv1.5 and Src. When hKv1.5 and associated proteins were immunoprecipitated from cell lysates with a specific antibody, Src was coprecipitated. Similarly, when Src and associated proteins were immunoprecipitated from HEK 293 cell lysates, hKv1.5 co-precipitated with endogenous and co-expressed Src. Expression of hKv1.5 protein was not altered by v-Src coexpression, as verified by protein immunoblot analysis of cell lysates with antibodies directed against tagged and native sequences of the channel. Furthermore, immunoblot or protein silver stain analysis of immunoprecipitates demonstrated that the efficiency of immunoprecipitation of hKv1.5 was not affected by v-Src coexpression. Enzymatic activity of Src also co-precipitated with hKv1.5, as detected by an in vitro kinase assay with hKv1.5 immunoprecipitates and a Src-specific substrate. The results of these experiments are summarized in Tables 2 and 3 in Example 1.

The association between hKv1.5 and Src was also observed in human tissue. Native Src was detected in immunoprecipitates, prepared with a hKv1.5 antiserum, from human myocardium ventricle tissue lysates. The native Src that co-immunoprecipitated with native hKv1.5 co-migrated on protein immunoblots with native Src, immunoprecipitated directly with a polyclonal anti-Src antibody. Thus, association of hKv1.5 and Src occurs under physiological conditions and does not depend on expression in a heterologous system. This association may contribute to the co-localization of hKv1.5 and Src in cellular adhesion zones in myocardium. Although the stoichiometry of the association between hKv1.5 and Src is not known, only a fraction of the total myocardial Src co-immunoprecipitated with hKv1.5, consistent with the fact that Src phosphorylates other substrates. The results of this study are summarized in Table 4 in Example 1.

There are specific sequence requirements for the association of hKv1.5 and Src. For example, the amino-terminal region of rat (rKv1.5) also contains a proline-rich motif. In contrast to hKv1.5, however, rKv1.5 failed to co-immunoprecipitate with Src. Thus, the association between channel and Src is observed only for the human isoform, possibly because its proline-rich binding sequence is preferred by the Src SH3 domain. These results are presented in Table 5 in Example 2.

The binding of hKv1.5 to the Src SH3 domain itself expressed as a fusion protein with glutathione S-transferase was also examined. Cell lysates prepared from vector control and hKv1.5 transfected cells were incubated with a GST protein containing the Src SH3 domain (GST—Src—SH3) or no insert (GST). The hKv1.5 protein was effectively precipitated by GST—Src—SH3 but not by GST. The specificity of this interaction was tested by the preabsorption of the fusion protein with a peptide containing the sequence of the proline-rich region of hKv1.5. Binding of hKv1.5 was attenuated by preabsorption of the fusion protein with the peptide. The direct binding of the Src SH3 domain to HKv1.5 was demonstrated in a filter binding assay (Far-western blot). GST—Src—SH3 bound to hKv1.5 on the filter, whereas no binding was detected with rKv1.5. The role of the proline-rich motif in the channel in the binding of GST—Src—SH3 to hKv1.5 was demonstrated further by the absence of filter binding after preabsorption of the GST—Src—SH3 with the peptide. The results of these experiments are summarized in Tables 6 and 7 in Example 2.

The hKv1.5 protein was tyrosine phosphorylated when it was co-expressed with v-Src. To determine whether co-expression of v-Src influenced channel activity, HKv1.5 macroscopic currents were measured in cell-attached membrane patches, with and without v-Src co-expression. Current through hKv1.5 channels was suppressed when the channel was coexpressed with v-Src even though channel protein expression was not altered. The results of this study are presented in Table 8 in Example 3 and in the FIGURE.

These results clearly show that Src associates with hKv1.5 via the interaction of the Src SH3 domain with the proline-rich binding region of the channel and that this targeting is important in the overall process of tyrosine phosphorylation of the channel. Further, the phosphorylation of hKv1.5 leads to diminished ion current through the channel.

The results presented herein, as well as the existence of proline-rich intracellular regions in a variety of ion channels, support the conclusion that the activity of many ion channels, and hence the ion conductivity or flux of a cell membrane, can be influenced by inhibiting or enhancing the formation of a complex between the channel and a protein tyrosine kinase, such as Src. Therefore, compounds which inhibit or enhance the formation of such a complex can be useful therapeutic agents for the alleviation of conditions in which ion conduction plays a role. Examples of conditions in which decreased potassium flux or conductance has been implicated include cardiac arrhythmia, episodic ataxia, and myokymia. Further, evidence points to the potential benefit of decreased potassium conduction in the enhancement of cognitive function in patients suffering from senility or Alzheimer's disease, while increasing potassium ion conductance may have therapeutic value in conditions such as stroke and trauma.

The mechanism described herein suggests that compounds which interact with an ion channel proline-rich binding sequence and/or a protein tyrosine kinase SH3 domain will effectively compete with the partner protein for the binding site and inhibit the formation of the channel-protein tyrosine kinase complex. Compounds which augment the association of the channel proline-rich binding sequence and the protein tyrosine kinase SH3 domain will enhance the formation of the complex.

The present invention provides a method for assessing the ability of a compound to modulate the binding of a protein tyrosine kinase to an ion channel. The method comprises the steps of (1) contacting a first polypeptide comprising the proline-rich binding region of the ion channel, a second polypeptide comprising the SH3 domain of the protein tyrosine kinase and a compound to be assessed (also referred to as "the test compound"); and (2) determining the extent of complex formation between the first polypeptide and the second polypeptide.

Either the first or second polypeptide can be incubated with the compound to be assessed before the other polypeptide is added to the system.

Preferably, the method is carried out in aqueous solution under physiological conditions, for example, physiological temperature and pH.

Modulation of the binding of a protein tyrosine kinase to an ion channel refers to the inhibition or enhancement of such binding. Thus, a compound which functions as either an agonist (enhancer) or antagonist (inhibitor) of the binding can be said to modulate the binding. A compound inhibits the binding when the presence of the compound decreases binding as compared to a control (such as when the polypeptides are contacted in the absence of the compound). A compound enhances binding if the amount of binding in the presence of the compound is greater than observed in a control.

Ion channels or sequences therefrom which can be used in this method include amino acid sequences comprising a proline-rich binding domain. The term "proline-rich binding domain", as used herein, refers to an amino acid sequence within the intracellular domain of the channel that includes several proline residues. In general, such a sequence comprises a sequence of the type —PXXP— as its core sequence, wherein each X is, independently, proline or a hydrophobic amino acid. Amino acid residues which flank this core sequence can also play a role in binding. Examples of such sequences have been observed in a variety of ion channels, including mammalian potassium channels, chloride channels, and glutamate receptors. In a preferred embodiment, the channel is a potassium channel. Examples of suitable channels and their proline-rich binding sequences are presented in the table below.

The proline-rich binding sequence can be a sequence found in an ion channel which is native to or derived from one or more of a variety of different tissues. For example, the presented in the table. For example, the polypeptide can be an intact potassium channel or a fragment of a potassium channel which includes the proline-rich binding region. Also included are fusion proteins which comprise a portion of the potassium channel amino acid sequence which includes the proline rich binding sequence fused to an additional peptide. Suitable ion channel fragments include portions of the ion channel amino acid sequence which include one or more of the sequences presented in Table 1. For example, when the ion channel is hKv1.5, a suitable fragment can comprise the sequence RPLPPLPDPGVRPLPPLPEELPRRP (SEQ ID NO:8).

TABLE 1

Mammalian ion channels with proline-rich PXXP motifs. The sequences, designated by their
GenBank/EMBL accession numbers, were retrieved from the NCBI Entrez database.

| Ion Channel | Accession No. | Proline-rich Sequence |
|---|---|---|
| K$^+$Channels | | |
| Shaker-related subfamily | | |
| Kv1.2 (human) | L02752 | $^{16}$PGHPQDTYDP (SEQ ID NO: 3), $^{436}$PKIPSSP (SEQ ID NO: 4) |
| Kv1.3 (rat) | X16001 | $^{35}$RYEPLPPALP (SEQ ID NO: 5) |
| Kv1.3 (human) | M55515 | $^{43}$RYEPLPPSLP (SEQ ID NO: 6) |
| HKv1.5 (rat) | M27158 | $^{65}$RPLPPMA (SEQ ID NO: 7) |
| HKv1.5 (human) | M55513 | $^{65}$RPLPPLPDPGVRPLPPLPEELPRRP (SEQ ID NO: 8) |
| Kv1.6 (human) | X17622 | $^{149}$KPLPSQP (SEQ ID NO: 9) |
| Shab-related subfamily | | |
| Kv2.1 (rat) | X16476 | $^{13}$PPEPMEIV (SEQ ID NO: 10), $^{562}$PSPVAPLP (SEQ ID NO: 11) |
| | | $^{576}$PTPLLP (SEQ ID NO: 12), $^{596}$PLPTSPKFRP (SEQ ID NO: 13) |
| Kv2.2 (rat) | M77482 | $^{21}$PPEPVEII (SEQ ID NO: 14), $^{619}$PLTPVP (SEQ ID NO: 15) |
| Shaw-related subfamily | | |
| Kv3.1 (rat) | M68880 | $^{461}$PRPPQLGSP (SEQ ID NO: 16) |
| Kv3.2 (rat) | M34052 | $^{56}$PLPPPLSPPPRPPPLSPVP (SEQ ID NO: 17) |
| | | $^{498}$PPAPLASSP (SEQ ID NO: 18), $^{550}$PPLSPPERLP (SEQ ID NO: 19) |
| Kv3.3 (rat) | M84210-1 | $^{33}$PAPTPQPPESSPPPLLPP (SEQ ID NO: 20) |
| | | $^{565}$PRPPQPGSPNYCKPDPPPPPPHP (SEQ ID NO: 21) |
| | | $^{597}$PPPPITPP (SEQ ID NO: 22), $^{615}$PPGPHTHP (SEQ ID NO: 23) |
| | | $^{638}$PPLPAPGEPCP (SEQ ID NO: 24) |
| Kv3.4 (human) | M64676 | $^{551}$PQWPREFPNGP (SEQ ID NO: 25) |
| Shal-related subfamily | | |
| Kv4.1 (mouse) | M64226 | $^{25}$QPLPPAP (SEQ ID NO: 26), $^{606}$PTPPANTPDESQPSSP (SEQ ID NO: 27) |
| Kv4.2 (rat) | S64320 | $^{21}$PAVSPMPAPP (SEQ ID NO: 28) |
| Kv4.3 (rat) | L48619 | $^{21}$PVANCPMPLAP (SEQ ID NO: 29) |
| Small K(Ca) channel subfamily | U69883 | $^{69}$PARPSPGSPRGQP (SEQ ID NO: 30), |
| hSK1 (human) | | $^{526}$RPPPPPLPPRPGPGP (SEQ ID NO: 31) |
| KvLQT subfamily | U70068 | $^{4}$PVSPAPAP (SEQ ID NO: 32) |
| KvLQT1 (mouse) | | |
| Glutamate Receptors | Q01097 | 1111RRPPRSP (SEQ ID NO: 33) |
| NMDA Receptors | Q01098 | $^{942}$PGPPGQPSPSGWRPP (SEQ ID NO: 34), |
| NMDA2B (mouse) | | $^{962}$PLARRAPQPPARPQP (SEQ ID NO: 35) |
| NMDA2C (mouse) | | $^{900}$PPAKPPPPPQPLPRPPPGPAP (SEQ ID NO: 36) |
| NMDA2D (rat) | L31612 | $^{926}$PLSPPTTQPPQKPPPPGFPSPPAPP (SEQ ID NO: 37) |
| Chloride Channels | | |
| CLC 0 (rat) | X56758 | $^{659}$PRPPSPVPAEEP (SEQ ID NO: 38) |
| CLC 1 (rat) | X62894 | $^{723}$PQTPTPPPPPPPPLPPQFPIAPSYPEEP (SEQ ID NO: 39) |
| CLC 2 (rat) | X64139 | $^{760}$PLKPALKRGP (SEQ ID NO: 40) | ion channel can be native to tissues such as cardiac tissue, blood (e.g., T cell), brain tissue, epithelial tissue, smooth muscle tissue, skeletal muscle tissue and progenitor tissue, such as bone marrow.

The polypeptide comprising an ion channel proline-rich binding domain can be any peptide which comprises a proline rich binding sequence from the amino terminus of a potassium channel, such as one of the proline-rich sequences The peptide comprising an SH3 domain can be any peptide which includes the amino acid sequence of a Src SH3 domain. For example, the peptide can be a Src protein or a fragment of a Src protein which includes the SH3 domain. Also included are fusion proteins comprising a Src fragment which includes the SH3 domain, fused to a second peptide. An example of a suitable fusion protein is GST—

Src—SH3, which comprises a glutathione S-transferase protein to which the Src SH3 domain has been covalently attached.

Fusion proteins comprising either the ion channel proline-rich binding sequence or the protein tyrosine kinase SH3 domain can include a second polypeptide which includes a sequence which is recognized by an antibody or is tagged with a label, such as a calorimetric or radioactive label, as is known in the art and described by Midgley et al. in Hartley, ed., *Cellular Interactions in Development,* IRL Press, Chapter 6 (1993). Fusion proteins can be conveniently made through known methods, such as recombinantly. Other fusion proteins which can be used possess essentially the amino acid sequence of the ion channel or the protein tyrosine kinase and have additional amino acids at one or both terminii which do not significantly alter or detract from the properties of the protein.

The extent of binding of the polypeptide comprising an ion channel proline-rich binding region to the polypeptide comprising the Src SH3 domain can be determined by a suitable protein-protein binding assay, such as are known in the art. For example, complex formation can be determined by a two-hybrid system, a yeast-based genetic assay for detecting protein-protein interactions (Fields et al., *Trends in Genetics* 10 : 286–292 (1994)). Another suitable method for determining the extent of protein—protein binding is co-immunoprecipitation, as is described in Example 1 and in Ransone, *Methods Enzymol.* 254 : 491 (1995)). In this method, an antibody which recognizes one of the proteins is added to the system to immunoprecipitate that protein. Co-precipitation of the potential binding partner, as determined, for example, by a functional assay, provides strong evidence for binding.

For a co-immunoprecipitation assay, antibodies raised to the first and/or second polypeptide can be used. Alternatively, one or both polypeptides can be tagged with an epitope. An antibody which recognizes the epitope can then be used to precipitate the tagged protein.

The ability of the test compound to modulate complex formation can be determined by comparing the extent of complex formation in the presence of the test compound to the extent of complex formation in the absence of the test compound. The ability of the test compound to modulate complex formation as a function of its concentration can also be determined by performing the assay at varying concentrations of the test compound.

The assay can be performed using polypeptides which are substantially pure, or can be performed using a cell lysate. For example, cells which express both a first polypeptide comprising the proline-rich binding region of the potassium channel and a second polypeptide comprising the SH3 domain of the protein tyrosine kinase can be lysed to form a solution comprising the two polypeptides. The compound to be assessed can then be added to the cell lysate and the extent of complex formation between the first and second polypeptides can be determined. The first and second polypeptides can be native to the cell or the cell can be a host cell expressing recombinant DNA which encodes the first polypeptide, the second polypeptide or both.

The first polypeptide or the second polypeptide can, optionally, be immobilized on a solid support, such as a silica gel support or a polymer support. The assay can also be performed in a solution, such as a cell lysate, which includes additional components, including, but not limited to ATP, cofactors, salts and buffers.

The method can also be performed in cell culture on intact cells. The first and second polypeptides can be native to the cells used or the cells can be recombinant cells comprising recombinant DNA which encodes the first polypeptide, the second polypeptide or both. The compound to be assess can be added to the cells and the extent of binding of the two polypeptides can be determined using methods suitable to whole cells, or the cells can be lysed prior to determining the extent of binding.

A variety of different cell types can be used. For example, the cells can be human embryonic cells, or the cells can come from tissues such as cardiac tissue, blood (e.g., T cell), brain tissue, epithelial tissue, smooth muscle tissue, skeletal muscle tissue and progenitor tissue, such as bone marrow. In one embodiment, the cells are human cardiac muscle cells.

Recombinant cells comprising recombinant DNA encoding a polypeptide comprising an ion channel proline-rich binding sequence, a polypeptide comprising a protein tyrosine kinase SH3 domain or both can be prepared by methods known in the art, such as the methods described in Sambrook et al., *Molecular Cloning: A Laboratory Manual,* 2nd Edition (Cold Spring harbor Laboratory, Cold Spring Harbor, N.Y. (1989)), incorporated herein by reference. For example, the cells can transfected with DNA encoding one or both polypeptides via a recombinant virus, such as cytomegalovirus, adenovirus, and vaccinia virus. The cells can also be transfected by lipofectamine transfection, electroporation or any other suitable method known in the art.

In another embodiment, the invention includes compounds which have been shown by the present method to modulate the binding of a protein tyrosine kinase to an ion channel. Such compounds can include small organic molecules, such as drugs and prodrugs, particularly compounds which can cross the cell membrane. Other examples are peptides and polypeptides, including peptidomimetics. For example, peptides and polypeptides which comprise either the proline-rich binding sequence of the ion channel or the SH3 domain of the protein tyrosine kinase may compete for binding with the intact protein (thereby inhibiting binding). Also included are antibody fragments, particularly antibody fragments which are sufficiently small to cross the cell membrane and include a variable region which is specific to the binding site of the ion channel or the protein tyrosine kinase.

The compounds which modulate the binding of a protein tyrosine kinase to an ion channel or modulate the ion channel, described above, can be used in the treatment of an ion channel-mediated condition in an animal by administering to the animal, for example, a human, a therapeutically effective amount of the compound or combination of compounds. Ion channel-mediated conditions which can be treated by this method have been discussed above, and include cardiac arrhythmia, episodic ataxia, myokymia, senility, Alzheimer's disease, stroke and trauma.

The quantity of an individual compound to be administered will be determined on an individual basis and will be determined, at least in part, by consideration of the individual's size, the severity of symptoms to be treated and the result sought. The agent may be administered alone or in a pharmaceutical composition comprising the agent and an acceptable carrier or diluent.

The compounds can be administered by subcutaneous or other injection, intravenously, topically, orally, parenterally, transdermally, or rectally, and can depend on the particulars of the disease to be treated and the nature of the compound. The form in which the agent will be administered, for example, powder, tablet, capsule, solution, or emulsion, will depend on the route by which it is administered. The therapeutically effective amount can be administered in a single dose or in a series of doses separated by appropriate time intervals, such as hours.

EXAMPLES

General Materials and Methods

The following procedures and materials were employed in Examples 1–3 below. Additional methods unique to a particular. Example are provided with that Example.

cDNA Expression Vectors

All mammalian expression vectors for these experiments contained the cytomegalovirus promoter upstream from the coding region. The plasmid pRc-CMV (Invitrogen, San Diego, Calif.) was used as control vector for all experiments. A vector encoding hKv1.5 fused to an epitope tag (18) was provided by L. Philipson (Univ. of Chicago), and one encoding v-Src was provided by R. Huganir (Johns Hopkins Univ., Baltimore, Md.).

Cell Culture and Transfection Procedures

Human embryonic kidney (HEK) cells were maintained in modified eagle medium (MEM) containing 2% penicillin/streptomycin and 10% fetal bovine serum (Gibco/BRL, Grand Island, N.Y.). Cells were grown to confluency over one week, dissociated with trypsin-EDTA and mechanical trituration, diluted in MEM to a concentration of approximately 600 cells/µl, and replated on Corning plastic dishes #25000. cDNAs coding for Kv1.3, v-src, EGFr or control vector were introduced into HEK 293 cells by lipofectamine transfection. Cells were transfected three to five days after recovery from cell passage, at 70–80% confluency. The total amount of cDNA used for transfection was the same for all control and experimental groups. Cells were transfected with 5 µg DNA/60 mm dish.

For Kv1.5/Src co-expression experiments, cells were transfected with a total of 10 µg DNA/60 mm dish, 5 µg DNA of each construct coding for Kv1.3 and tyrosine kinases. The potassium ion channel or tyrosine kinases alone groups were brought up to 10 µg DNA by the addition of 5 µg vector-control DNA. Co-transfection control cells were transfected with 10 µg vector noncoding DNA/60 mm dish. Cells were incubated for 5 hours with the lipofectamine/DNA mixture diluted in serum-reduced medium (OptiMEM, Gibco/BRL, Grand Island, N.Y.). Transfection efficiency was monitored in parallel plates by staining for the β-galactosidase reaction product in Lac-Z expression plasmid transfected cells. Staining efficiency (blue cells) normally ranged from 70–90%. Expression of Kv1.5 could be detected immunochemically in as little as 24 hours and was sufficient to produce macroscopic currents in cell-attached membrane patches 24–72 hours after transfection.

Cell Lysis and Immunoprecipitation

Cells were harvested two days after transfection by lysis in ice-cold 1% Triton X-100 modified immunoprecipitation buffer containing protease and phosphatase inhibitors (25 mM Tris, pH 7.5; 150 mM NaCl; 100 mM NaF; 5 mM EDTA; 1 mM $Na_3VO_4$, 1% Triton X-100; 1 mM PMSF; 1 µg/mL leupeptin; 2 µg/mL aprotinin). The cell lysates were clarified by centrifugation (15,000 x g, 5 min., 4° C.). Immunoprecipitation of lysate proteins from the supernatant utilized a 2 hour incubation with antibody at 4° C. followed by an overnight incubation with Protein-A sepharose. The immunoprecipitates were washed 3 times with ice-cold 0.1% Triton X-100 modified immunoprecipitation buffer. Lysate samples and washed immunoprecipitates were diluted in SDS-gel loading buffer.

Western Blot and Autoradiogram Procedures

Proteins were separated on 10% acrylamide gels by SDS-PAGE and electrotransferred to nitrocellulose blots. The blots were blocked in 5% nonfat milk and incubated overnight in primary antibody at 4° C. The blots were incubated with horseradish peroxidase-conjugated secondary antibody (Amersham Corp., Arlington Heights, Ill.) for two hours at room temperature. Enhanced chemiluminescence exposure on XAR film was used to visualize labelled protein. The magnitude of the signal is directly related to the amount of HRP-conjugated secondary antibody. The film autoradiograms were analyzed by densitometry using a Biorad model GS-670 Imaging Densitometer. Relative densitometry values were shown to be linear by serial dilution of protein samples used for western immunoblotting.

Antibodies and Reagents

Tyrosine-phosphorylated proteins were immunoprecipitated and detected by western blot with mouse monoclonal antibody 4G10 (Upstate Biochemical). The specificity of 4G10 was verified by preabsorption with phosphotyrosine. Tyrosine, phosphoserine and phosphothreonine did not affect anti-phosphotyrosine immunostaining. The antiphosphotyrosine antibody PY20 was used for western blot to detect tyrosine-phosphorylated proteins in the 4G10 immunoprecipitates. Immunoprecipitated tyrosine phosphorylated proteins were further characterized by alkaline phosphatase treatment. Src expression (v-src and c-src) was detected with a mouse monoclonal antibody. All other chemicals used for western blotting, immunoprecipitation and electrophysiology were purchased from Sigma Chemical Company (St.Louis, Mo.).

Example 1 Co-immunoprecipitation of hKv1.5 and Src

Proteins were immunoprecipitated overnight at 4° C. from lysates with 4 µg of primary antibody and 26 µl of protein A/G(Pierce, Rockford, Ill.) per 400 µg of lysate protein. The lysates and washed immunoprecipitated proteins were separated by SDS-polyacrylamide gel electrophoresis (PAGE), and protein immunoblots were probed with an antibody that recognizes both rKv1.5 and hKv1.5 (anti-Kv1.5; provided by J. Trimmer (State Univ. of New York, Stony Brook, N.Y.)], an antibody to an epitope tag sequence fused to hKv1.5 (anti-tag-hKv1.5; provided by L. Philipson), or antibody to Src (MAB 327; Oncogene Science, Cambridge, Mass.). Antibody binding was visualized by enhanced chemiluminescence (ECL; Amersham, Arlington Heights, Ill.). Silver stain was used to detect immunoprecipitated proteins separated by SDS-PAGE. Src activity was measured under standard conditions with the substrate G10A, a GST fusion protein that contains an Src SH3 domain binding motif and a tyrosine phosphorylation site (Alexandropoulos, K., et al., *Proc. Natl. Acad. Sci., U.S.A.,* 92: 3110 (1995)). The reaction products were separated by SDS-PAGE, and protein immunoblots were probed with an antibody to phosphotyrosine (4G10; Upstate Biotechnology, Lake Placid, N.Y.) and visualized by ECL.

HEK 293 cells were transfected with CMV vector with no Insert (control), vector encoding v-Src, vector encoding hKv1.5, or two separate vectors, one encoding hKv1.5 and the other encoding v-Src. Expression of hKv1.5 was measured on protein immunoblots of cell lysates probed with anti-tag-hKv1.5. Densitometry of autoradiograms was used to quantitate channel expression. For each experiment, the density (expression level) of hKv1.5 transfected alone was set to 1. When Src was cotransfected, the relative density of hKv1.5 was 0.98±0.05 (mean±SEM; n=9; not significant by t-test). Immunoblot analysis of anti-tag-hKv1.5 Immunoprecipitates (IP) with anti-tag-hKv1.5 probe confirmed that the efficiency of Immunoprecipitation of hKv1.5 (density set to 1) was not affected by coexpression of v-Src (relative density 1.06±0.10; n=B; not. significant by t-test). Src that co-immunoprecipitated with hKv1.5 was detected by probing anti-tag-hKv1.5 IP with anti-Src. The hKv1.5 that co-immunoprecipitated with endogenous c-Src and expressed v-Src was detected by probing anti-Src IP with anti-tag-hKv1.5.

In a second experiment, HEK293 cells were transfected as described above. Anti-tag-hKv1.5 IP were assayed for Src activity by Incubation with or without the Src substrate fusion protein G10A. The reaction products were separated on protein immunoblots that were probed with antibody 4G10 to phosphotyrosine (n=4). Native Src that co-Immunoprecipitated with native Kv1.5, or was immunoprecipitated directly with anti-Src, was detected by probing IP prepared from human myocardium tissue lysates (separated on Immunoblots) with anti-Src (n=4). IP with an antiserum against Kv1.3, another potassium channel, was used as an additional control.

The results of these experiments are summarized in Tables 2, 3 and 4, below. In each table the signal detected is indicated by "−" (no signal), "+" (weak signal) or "+++" (strong signal). The results presented in Table 2 demonstrate co-immunoprecipitation of hKv1.5 and Src from transfected cells. The results presented in Table 3 show that Src activity co-immunoprecipitates with hKv1.5. Table 4 shows that native Src from human myocardium co-immunoprecipitates with hKv1.5 from the same tissue.

TABLE 2

| Transfection Condition: | Control | v-Src | hKv1.5 | hKv1.5 + v-Src |
|---|---|---|---|---|
| CELL LYSATES BLOT: Anti-tag-hKv1.5 | − | − | +++ | +++ |
| IP:Anti-tag-hKv1.5 BLOT: Anti-tag-hKv1.5 | − | − | +++ | +++ |
| IP:Anti-tag-hKv1.5 BLOT: Anti-Src | − | − | − | +++ |
| IP:Anti-Src BLOT: Anti-tag-hKv1.5 | − | − | + | +++ |

TABLE 3

| Transfection Condition: | Control | v-Src | hKv1.5 | hKv1.5 + v-Src |
|---|---|---|---|---|
| IP: Anti-tag-hKv1.5 ASSAY: Src Kinase Assay BLOT: Anti- | −− | −− | −− | +++ |

TABLE 3-continued

| Transfection Condition: | Control | v-Src | hKv1.5 | hKv1.5 + v-Src |
|---|---|---|---|---|
| Phosphotyrosine Assay IP −/+ Src Substrate: | −+ | −+ | −+ | −+ |

TABLE 4

| IP Antiserum: | Control Serum | Anti-Kv1.3 | Anti-Kv1.5 | Anti-Src |
|---|---|---|---|---|
| IP: Rabbit antisera BLOT: Anti-Src | − | − | + | +++ |

Example 2 Identification of Domains that Mediate Binding of hKv1.5 and Src

HEK 293 cells were transfected using standard methodology. The CMV vector encoding rKv1.5 was provided by J. Trimmer. For fusion protein precipitation experiments cell lysates were incubated overnight at 4° C. with GST fusion protein (1.0 µg/ml of cell lysate). The GST fusion proteins and bound proteins were separated from unbound protein by incubation with glutathione-agarose beads. Where indicated, GST fusion proteins were preabsorbed by incubating with 100 times greater concentration of peptide $NH_2$—SGVRPLPPLPDPGVRPLPPLPS—COOH (peptide hKv1.5$_{62-83}$; Bio-Synthesis, Louisville, Tex.). The proteins bound to the washed agarose beads were separated by SDS-PAGE, and immunoblots were probed with anti-tag-hKv1.5.

HEK 283 cells were transfected with CMV vector with no insert (control), vector encoding v-Src, vector encoding hKv1.5 or rKv1.5, or two separate vectors, one encoding hKv1.5 or rKv1.5 and the other encoding v-Src. Expression of hKv1.5 and rKv1.5 was detected in cell lysates by protein immunoblotting with anti-Kv1.5 (Maletic-Savatic, M., et al., *J. Neurosci.*, 15: 3840 (1995)), which recognizes both channels. Anti-Src IP, separated on Immunoblots, were probed with anti-Kv1.5.

HEK 293 cells were transfected with CMV vectors coding for vector with no insert (control) or hKv1.5. Expression of hKv1.5 was confirmed by immunoblotting the cell lysates with anti-tag-hKv1.5. Cell lysates were incubated with GST alone or GST fusion protein containing the Src SH3 domain (GST—Src—SH3) (Ren, R., et al., *Science*, 259: 1157 (1993)), with or without fusion protein preabsorption with a peptide corresponding to the proline-rich sequence comprising amino acids 62 through 83 of hKv1.5 (peptide hKv1.5$_{62-83}$). Proteins bound to GST fusion proteins were separated by SDS-PAGE, and immunoblots were probed with anti-tag-hKv1.5 (bottom panel) (n=4). (C) Far-western blots were prepared with anti-Kv1.5 IP from cells transfected with hKv1.5 or rKv1.5. The blots were probed with biotinylated GST—Src—SH3 (1 µg/ml) (Ren, R., et al., *Science*, 259: 1157 (1993)) or biotinylated GST—Src—SH3 reabsorbed with peptide hKv1.5$_{62-83}$. The blots were then incubated with avidin-horseradish peroxidase, and bound fusion protein was visualized by ECL (n=4).

The results of these experiments are presented in Tables 5, 6, and 7 below. In each table the signal detected is indicated by "−" (no signal), "+" (weak signal) or "+++" (strong signal). Table 5 demonstrates that Src co-immunoprecipitates with hKv1.5 from transfected cells, but not with rKv1.5. The results presented in Table 6 demonstrate that hKv1.5 coprecipitates with a fusion protein comprising the Src SH3 domain. Table 7 shows that hKv1.5 binds directly to a fusion protein containing the Src SH3 domain.

TABLE 5

| Transfection condition | control | v-Src | hKv1.5 | hKv1.5 + v-Src | rKv1.5 | rKv1.5 + v-Src |
|---|---|---|---|---|---|---|
| Cell Lysates BLOT: Anti-Kv1.5 | − | − | + | + | +++ | +++ |
| IP:Anti-Src BLOT: Anti-Kv1.5 | − | − | + | +++ | − | − |

TABLE 6

| Transfection condition | control | con-trol | hKv1.5 | hKv1.5 | hKv1.5 | hKv1.5 |
|---|---|---|---|---|---|---|
| Cell Lysates BLOT: Anti-tag-hKv1.5 | − | − | +++ | +++ | +++ | +++ |
| GST Fusion Protein Precipitation BLOT: Anti-tag-hKv1.5 | − | − | − | − | + | + |
| GST fusion protein | GST | GST-Src-SH3 | GST | GST | GST-Src-SH3 | GST-Src-SH3 |
| peptide preabsorption | − | − | − | + | − | + |

TABLE 7

| Transfection condition | control | rKv1.5 | hKv1.5 |
|---|---|---|---|
| IP: Anti-Kv1.5 Far Western Blot: Src-SH3 | − | − | +++ |
| IP: Anti-Kv1.5 Far Western Blot: GST-Src-SH3 + Peptide | − | − | − |

Example 3 Tyrosine Phosphorylation of hKv1.5 and Suppression of Channel Current by Coexpression with v-Src Patch-clamp recordings of macroscopic currents were made in the cell-attached patch configuration. Patches were held at =90 mV and stepped to depolarizing potentials in 5-mV increments to 0 mV. The pulse duration was 400 ms and the interpulse interval was 10 s.

HEK 293 cells were transfected with CMV vectors; vector with no insert (control); v-Src; hKv1.5; or one vector encoding hKv1.5 and another encoding v-Src. Cells were lysed, and proteins were immunoprecipitated with anti-tag-hKv1.5. IP were separated by SDS-PAGE, and protein was detected by silver stain, immunoblots were probed with antibody 4G10 to phosphotyrosine (n=4). HEK 293 cells were transfected with a CMV vector encoding hKv1.5 or one vector encoding hKv1.5 and another encoding v-Src. Macroscopic currents evoked by a series of depolarizing voltage pulses were recorded from cell-attached membrane patches 2 days after transfection. The peak current at +40 mV was 592±163 pA (mean±SEM; n=8) in patches from cells expressing hKv1.5 alone, and 27±15 pA (n=9) in patches from cells coexpressing v-Src (significantly different, $P<0.02$, t-test).

The FIGURE is a graph displaying the relative potassium ion conductance of HEK 293 cells expressing hKv1.5 alone and cells expressing both hKv1.5 and Src. The results presented in Table 8 show that hKv1.5 is tyrosine phosphorylated when cotransfected with Src. The strength of the signal detected is indicated by "−" (no signal), "+" (weak signal) or "+++" (strong signal).

TABLE 8

| Transfection condition | control | v-src | hKv1.5 | hKv1.5 + V-Src |
|---|---|---|---|---|
| IP: Anti-tag-hKv1.5 Silver Stain, hKv1.5 protein | − | − | +++ | +++ |
| IP: Anti-tag-hKv1.5 BLOT: Anti-PY | − | − | − | +++ |

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A method for determining if a compound modulates the binding of a potassium ion channel to the SH3 domain of a protein tyrosine kinase, wherein said potassium ion channel binds to said protein tyrosine kinase, comprising the steps of:

(a) contacting the potassium ion channel with a polypeptide comprising the SH3 domain of the protein tyrosine kinase;

(b) contacting the potassium ion channel with the compound to be assessed; and (c) measuring the extent of binding of the potassium ion channel and polypeptide comprising the SH3 domain of the protein tyrosine kinase wherein if the extent of binding is greater or less in the presence of the compound than the extent of binding in the absence of the compound, the compound modulates the binding of a potassium ion channel to the SH3 domain of a protein tyrosine kinase.

2. The method of claim 1 wherein the potassium ion channel is selected from the group consisting of Kv1.2, Kv1.3, Kv1.6, Kv3.1, Kv3.4, Kv4.1 and Kv4.3.

3. The method of claim 1 wherein the polypeptide comprises the SH3 domain of Src.

4. The method of claim 3 wherein the polypeptide is Src.

5. The method of claim 1 wherein the extent of binding of the potassium ion channel and the polypeptide comprising the SH3 domain of a protein tyrosine kinase is measured by co-immunoprecipitation or a two-hybrid system assay.

6. The method of claim 1 wherein the potassium ion channel is Kv1.5 and the protein tyrosine kinase is Src.

* * * * *

SEQUENCE LISTING

<160> NUMBER OF SEQ ID NOS: 41

<210> SEQ ID NO 1
<211> LENGTH: 4
<212> TYPE: PRT
<213> ORGANISM: Artificial Sequence
<220> FEATURE:
<223> OTHER INFORMATION: Consensus Sequence
<223> OTHER INFORMATION: Xaa in each sequence equals any amino acid residue

<400> SEQUENCE: 1

Pro Xaa Xaa Pro
1

<210> SEQ ID NO 2
<211> LENGTH: 7
<212> TYPE: PRT
<213> ORGANISM: Artificial Sequence
<220> FEATURE:
<223> OTHER INFORMATION: Consensus Sequence
<223> OTHER INFORMATION: Xaa in each sequence equals any amino acid
       residue

<400> SEQUENCE: 2

Arg Pro Leu Pro Xaa Xaa Pro
1               5

<210> SEQ ID NO 3
<211> LENGTH: 10
<212> TYPE: PRT
<213> ORGANISM: Homo sapien

<400> SEQUENCE: 3

Pro Gly His Pro Gln Asp Thr Tyr Asp Pro
1               5                   10

<210> SEQ ID NO 4
<211> LENGTH: 7
<212> TYPE: PRT
<213> ORGANISM: Homo sapien

<400> SEQUENCE: 4

Pro Lys Ile Pro Ser Ser Pro
1               5

<210> SEQ ID NO 5
<211> LENGTH: 10
<212> TYPE: PRT
<213> ORGANISM: Rat

<400> SEQUENCE: 5

Arg Tyr Glu Pro Leu Pro Pro Ala Leu Pro
1               5                   10

<210> SEQ ID NO 6
<211> LENGTH: 10
<212> TYPE: PRT
<213> ORGANISM: Homo sapien

<400> SEQUENCE: 6

Arg Tyr Glu Pro Leu Pro Pro Ser Leu Pro
1               5                   10

<210> SEQ ID NO 7
<211> LENGTH: 7
<212> TYPE: PRT
<213> ORGANISM: Rat

<400> SEQUENCE: 7

Arg Pro Leu Pro Pro Met Ala
1               5

<210> SEQ ID NO 8
<211> LENGTH: 25

-continued

<212> TYPE: PRT
<213> ORGANISM: Homo sapien

<400> SEQUENCE: 8

Arg Pro Leu Pro Pro Leu Pro Asp Pro Gly Val Arg Pro Leu Pro Pro
1               5                   10                  15
Leu Pro Glu Glu Leu Pro Arg Arg Pro
            20                  25

<210> SEQ ID NO 9
<211> LENGTH: 7
<212> TYPE: PRT
<213> ORGANISM: Homo sapien

<400> SEQUENCE: 9

Lys Pro Leu Pro Ser Gln Pro
1               5

<210> SEQ ID NO 10
<211> LENGTH: 8
<212> TYPE: PRT
<213> ORGANISM: Rat

<400> SEQUENCE: 10

Pro Pro Glu Pro Met Glu Ile Val
1               5

<210> SEQ ID NO 11
<211> LENGTH: 8
<212> TYPE: PRT
<213> ORGANISM: Rat

<400> SEQUENCE: 11

Pro Ser Pro Val Ala Pro Leu Pro
1               5

<210> SEQ ID NO 12
<211> LENGTH: 6
<212> TYPE: PRT
<213> ORGANISM: Rat

<400> SEQUENCE: 12

Pro Thr Pro Leu Leu Pro
1               5

<210> SEQ ID NO 13
<211> LENGTH: 10
<212> TYPE: PRT
<213> ORGANISM: Rat

<400> SEQUENCE: 13

Pro Leu Pro Thr Ser Pro Lys Phe Arg Pro
1               5                   10

<210> SEQ ID NO 14
<211> LENGTH: 8
<212> TYPE: PRT
<213> ORGANISM: Rat

<400> SEQUENCE: 14

Pro Pro Glu Pro Val Glu Ile Ile
1               5

<210> SEQ ID NO 15
<211> LENGTH: 6

```
<212> TYPE: PRT
<213> ORGANISM: Rat

<400> SEQUENCE: 15

Pro Leu Thr Pro Val Pro
 1               5

<210> SEQ ID NO 16
<211> LENGTH: 9
<212> TYPE: PRT
<213> ORGANISM: Rat

<400> SEQUENCE: 16

Pro Arg Pro Pro Gln Leu Gly Ser Pro
 1               5

<210> SEQ ID NO 17
<211> LENGTH: 19
<212> TYPE: PRT
<213> ORGANISM: Rat

<400> SEQUENCE: 17

Pro Leu Pro Pro Pro Leu Ser Pro Pro Arg Pro Pro Pro Leu Ser
 1               5                  10                  15

Pro Val Pro

<210> SEQ ID NO 18
<211> LENGTH: 9
<212> TYPE: PRT
<213> ORGANISM: Rat

<400> SEQUENCE: 18

Pro Pro Ala Pro Leu Ala Ser Ser Pro
 1               5

<210> SEQ ID NO 19
<211> LENGTH: 10
<212> TYPE: PRT
<213> ORGANISM: Rat

<400> SEQUENCE: 19

Pro Pro Leu Ser Pro Pro Glu Arg Leu Pro
 1               5                  10

<210> SEQ ID NO 20
<211> LENGTH: 18
<212> TYPE: PRT
<213> ORGANISM: Rat

<400> SEQUENCE: 20

Pro Ala Pro Thr Pro Gln Pro Pro Glu Ser Ser Pro Pro Pro Leu Leu
 1               5                  10                  15

Pro Pro

<210> SEQ ID NO 21
<211> LENGTH: 24
<212> TYPE: PRT
<213> ORGANISM: Rat

<400> SEQUENCE: 21

Pro Arg Pro Pro Gln Pro Gly Ser Pro Asn Tyr Cys Lys Pro Asp Pro
 1               5                  10                  15

Pro Pro Pro Pro Pro Pro His Pro
                20
```

```
<210> SEQ ID NO 22
<211> LENGTH: 8
<212> TYPE: PRT
<213> ORGANISM: Rat

<400> SEQUENCE: 22

Pro Pro Pro Pro Ile Thr Pro Pro
 1               5

<210> SEQ ID NO 23
<211> LENGTH: 8
<212> TYPE: PRT
<213> ORGANISM: Rat

<400> SEQUENCE: 23

Pro Pro Gly Pro His Thr His Pro
 1               5

<210> SEQ ID NO 24
<211> LENGTH: 11
<212> TYPE: PRT
<213> ORGANISM: Rat

<400> SEQUENCE: 24

Pro Pro Leu Pro Ala Pro Gly Glu Pro Cys Pro
 1               5                  10

<210> SEQ ID NO 25
<211> LENGTH: 11
<212> TYPE: PRT
<213> ORGANISM: Homo sapien

<400> SEQUENCE: 25

Pro Gln Trp Pro Arg Glu Phe Pro Asn Gly Pro
 1               5                  10

<210> SEQ ID NO 26
<211> LENGTH: 7
<212> TYPE: PRT
<213> ORGANISM: Mouse

<400> SEQUENCE: 26

Gln Pro Leu Pro Pro Ala Pro
 1               5

<210> SEQ ID NO 27
<211> LENGTH: 16
<212> TYPE: PRT
<213> ORGANISM: Mouse

<400> SEQUENCE: 27

Pro Thr Pro Pro Ala Asn Thr Pro Asp Glu Ser Gln Pro Ser Ser Pro
 1               5                  10                  15

<210> SEQ ID NO 28
<211> LENGTH: 10
<212> TYPE: PRT
<213> ORGANISM: Rat

<400> SEQUENCE: 28

Pro Ala Val Ser Pro Met Pro Ala Pro Pro
 1               5                  10

<210> SEQ ID NO 29
```

<211> LENGTH: 11
<212> TYPE: PRT
<213> ORGANISM: Rat

<400> SEQUENCE: 29

Pro Val Ala Asn Cys Pro Met Pro Leu Ala Pro
1               5                   10

<210> SEQ ID NO 30
<211> LENGTH: 13
<212> TYPE: PRT
<213> ORGANISM: Homo sapien

<400> SEQUENCE: 30

Pro Ala Arg Pro Ser Pro Gly Ser Pro Arg Gly Gln Pro
1               5                   10

<210> SEQ ID NO 31
<211> LENGTH: 15
<212> TYPE: PRT
<213> ORGANISM: Homo sapien

<400> SEQUENCE: 31

Arg Pro Pro Pro Pro Pro Leu Pro Pro Arg Pro Gly Pro Gly Pro
1               5                   10                  15

<210> SEQ ID NO 32
<211> LENGTH: 8
<212> TYPE: PRT
<213> ORGANISM: Mouse

<400> SEQUENCE: 32

Pro Val Ser Pro Ala Pro Ala Pro
1               5

<210> SEQ ID NO 33
<211> LENGTH: 7
<212> TYPE: PRT
<213> ORGANISM: Mouse

<400> SEQUENCE: 33

Arg Arg Pro Pro Arg Ser Pro
1               5

<210> SEQ ID NO 34
<211> LENGTH: 15
<212> TYPE: PRT
<213> ORGANISM: Mouse

<400> SEQUENCE: 34

Pro Gly Pro Pro Gly Gln Pro Ser Pro Ser Gly Trp Arg Pro Pro
1               5                   10                  15

<210> SEQ ID NO 35
<211> LENGTH: 15
<212> TYPE: PRT
<213> ORGANISM: Mouse

<400> SEQUENCE: 35

Pro Leu Ala Arg Arg Ala Pro Gln Pro Pro Ala Arg Pro Gln Pro
1               5                   10                  15

<210> SEQ ID NO 36
<211> LENGTH: 21
<212> TYPE: PRT
<213> ORGANISM: Mouse

```
<400> SEQUENCE: 36

Pro Pro Ala Lys Pro Pro Pro Pro Gln Pro Leu Pro Arg Pro Pro
 1               5                  10                  15

Pro Gly Pro Ala Pro
            20

<210> SEQ ID NO 37
<211> LENGTH: 25
<212> TYPE: PRT
<213> ORGANISM: Rat

<400> SEQUENCE: 37

Pro Leu Ser Pro Pro Thr Thr Gln Pro Pro Gln Lys Pro Pro Pro
 1               5                  10                  15

Gly Phe Pro Ser Pro Pro Ala Pro Pro
            20                  25

<210> SEQ ID NO 38
<211> LENGTH: 12
<212> TYPE: PRT
<213> ORGANISM: Rat

<400> SEQUENCE: 38

Pro Arg Pro Pro Ser Pro Val Pro Ala Glu Glu Pro
 1               5                  10

<210> SEQ ID NO 39
<211> LENGTH: 28
<212> TYPE: PRT
<213> ORGANISM: Rat

<400> SEQUENCE: 39

Pro Gln Thr Pro Thr Pro Pro Pro Pro Pro Pro Pro Leu Pro Pro
 1               5                  10                  15

Gln Phe Pro Ile Ala Pro Ser Tyr Pro Glu Glu Pro
            20                  25

<210> SEQ ID NO 40
<211> LENGTH: 10
<212> TYPE: PRT
<213> ORGANISM: Rat

<400> SEQUENCE: 40

Pro Leu Lys Pro Ala Leu Lys Arg Gly Pro
 1               5                  10

<210> SEQ ID NO 41
<211> LENGTH: 22
<212> TYPE: PRT
<213> ORGANISM: Homo sapien

<400> SEQUENCE: 41

Ser Gly Val Arg Pro Leu Pro Pro Leu Pro Asp Pro Gly Val Arg Pro
 1               5                  10                  15

Leu Pro Pro Leu Pro Ser
            20
```